United States Patent [19]

Dunlop et al.

[11] 3,977,981
[45] Aug. 31, 1976

[54] INHIBITING CORROSION WITH MACROCYCLIC TETRAMINE CORROSION INHIBITORS

[75] Inventors: Arthur K. Dunlop, Houston, Tex.; Janis Vasilevskis, West Caldwell, N.J.

[73] Assignee: Shell Oil Company, Houston, Tex.

[22] Filed: Nov. 14, 1975

[21] Appl. No.: 632,035

[52] U.S. Cl. .......................... 252/8.55 E; 21/2.7 R; 252/390; 252/394; 260/239 BC
[51] Int. Cl.² .................... C09K 7/02; C23F 11/00; C07D 257/00
[58] Field of Search............ 21/2.7 R; 252/390, 394, 252/8.55 E; 260/239 BC

[56] References Cited
UNITED STATES PATENTS

| | | | |
|---|---|---|---|
| 2,676,150 | 4/1954 | Loughran et al. | 252/394 X |
| 3,553,101 | 1/1971 | Foroulis | 252/390 X |
| 3,790,496 | 2/1974 | Hausler | 252/390 X |
| 3,907,578 | 9/1975 | Scherrer et al. | 252/390 X |

OTHER PUBLICATIONS

Curtis, "Some Cyclic Tetra-mines and Their Metal-Ion Complexes, Part I", Journal of the Chemical Society, London, Part III, pp. 2489–3512, 1964, No. 507, pp. 2644–2650.

Warner et al., "The Stereoisomers of a Macrocyclic Nickel(II) Complex Containing Six Asymmetric Centers", J. American Chem. Soc. vol. 91, No. 14, 1969, pp. 4092–4101.

*Primary Examiner*—Morris O. Wolk
*Assistant Examiner*—Arnold Tork

[57] ABSTRACT

Corrosion of corrodible metal material is prevented by contacting the material with an effective amount of a macrocyclic tetramine.

6 Claims, No Drawings

INHIBITING CORROSION WITH MACROCYCLIC TETRAMINE CORROSION INHIBITORS

BACKGROUND OF THE INVENTION

This invention relates to inhibiting corrosion. In one aspect it provides compositions and procedures for coating well conduits with an absorbed corrosion inhibiting compound.

Prior corrosion inhibiting processes include uses of various nitrogen-containing compounds to contact corrodible netal materials, such as well conduits, with film-forming materials capable of neutralizing acidic corrosive fluids. U.S. Pat. No. 3,770,055 describes uses of film-forming nitrogen-containing compounds in combination with pyridine. U.S. Pat. No. 3,654,993, which describes the incorporation of a corrosion inhibitor in a precipitate formed within a reservoir, indicates that there are so many known corrosion inhibitors that it is substantially impossible to describe them all. U.S. Pat. No. 3,200,071 describes uses of a mixture of a hydroxyaliphatic cyclic amidine, a cycloaliphatic amine and an aryl sulfonic acid. U.S. Pat. No. 3,623,979 describes uses of amide condensation products of polymeric acids and 1-aminoalkyl-2-imidazoline and discusses the complexity of the corrosion problem and corrsion prevention.

SUMMARY OF THE INVENTION

This invention relates to inhibiting the corrosion of a corrodible metal material. The corridible material is protected by contacting it with an effective amount of macrocyclic tetramine.

DESCRIPTION OF THE INVENTION

As used herein macrocyclic tetramine (MCTA) refers to a compound in which four nitrogen atoms and ten or twelve carbon atoms are connected into a 14-membered or 16-membered heterocyclic ring with the remaining valances of those atoms being satisfied by hydrogen atoms, multiple bonds, hydrocarbon radicals, or substituted hydrocarbon radicals.

The MCTA's which are suitable for use in this invention have the following skeletal formulas:

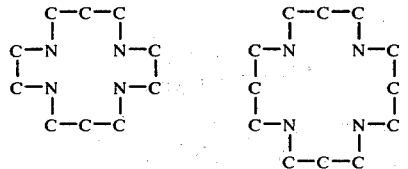

This invention is, at least in part, premised on the discovery that such macrocyclic tetramines are capable of providing significant amounts of corrosin inhibition. Comparative tests have indicated that such macrocyclic tetramines have properties inclusive of corrosion inhibiting efficiency, temperature stability, solubility characteristics in corrosive fluids, which are as good or better than those of corrosion inhibiting materials which are conventionally used.

Known methods can be used for preparing MCTA's suitable for use in the present invention. For example, such MCTA's can be prepared by condensing amines with aldehydes or ketones in the presence of nickel or copper salts as described by N.F. Curtis, Journal of Chemical Society, pages 2644 – 2650 (1964).

The amines used to prepare MCTA's suitable for use in the present invention are preferably diamines or tetramines in which pairs of nitrogen atoms are separated by chains of two or three carbon atoms. Particularly suitable amines include ethylenediamine, triethylenetetramine, phenylenediamine, and trimethylenediamine. Hydrocarbon-substituted homologs of such amines are generally suitable. The MCTA's containing 14-membered heterocyclic rings are prepared from amines in which the nitrogen atoms are separated by chains of two carbon atoms and the 16-membered MCTA's are prepared from those in which the nitrogen atoms are separated by chains of three carbon atoms.

The 14- and 16-membered MCTA's have been found to be relatively stable at relatively high temperatures, such as those likely to be encountered in the boreholes of deep oil or gas wells. Although it is likely that macrocyclic tetramines having larger rings can be prepared (or isolated from natural products), the relatively high thermal and chemical stability properties, combined with a significant corrosion preventing efficiency, cause the 14- and 16-membered MCTA's to be particularly advantageous as corrosion inhibitors.

The detailed mechanics of the inhibiting of acidic corrosion by a basic nitrogen-compound are not understood. However, it has been observed that the amount of inhibition increases with increases in the strength by which the basic nitrogen-compound is adsorbed on the metal (the surfaces of which may have been converted to the oxides or sulfides of that metal).

Relative to the present MCTA's the strength of their adsorption on metal increases with increases in the base strength of their nitrogen atoms. Since the 16-membered MCTA's are relatively very strongly basic secondary amines, they and their substitution products are particularly preferred for use in the present invention.

The MCTA's used in the present invention may contain substantially any hydrocarbon group or substituted-hydrocarbon group capable of replacing hydrogen atoms of a saturated unsubstituted MCTA or adding to a multiple bond of an unsaturated unsubstituted MCTA. Particularly suitable substituents include alkyl groups and mono or polyaminoalkyl groups having their carbon chains attached to one or more carbon or nitrogen atoms of the MCTA, or carboxyalkyl groups having their carboxy carbon atoms condensed with nitrogen atoms of the MCTA to form amide linkages. Particularly suitable sources of alkyl carboxy groups include the fatty acids from animal and vegetable oils such as the tallow, fish, cocoa, soya, tall oils, or the like oils. The dimeric and trimeric polyunsaturated fatty acids and the naphthenic acids, from mineral oil sources, and the like, are also suitable. In general, the chain lengths of such substituent groups can range from about 1 to 30 carbon atoms.

In general, the MCTA's having relatively low molecular weights and/or unsubstituted amino groups are particularly useful where at least some water solubility is desirable. Particularly where a preferential oil solubility is desirable, preferred classes of MCTA's include: (1) C-alkylated saturated MCTA's in which (a) the carbon and nitrogen atoms in the ring are joined by single bonds, (b) the remaining nitrogen atom valancies are satisfied by hydrogen atoms, and (c) the remaining carbon atom valancies are satisfieid by both hydrogen atoms and hydrocarbon radicals (commonly with 14 or 18 hydrogen atoms and six methyl groups); (2) analogous unsaturated C-alkylated MCTA's containing multiple bonds between at least one pair of ring carbon or nitrogen atoms; (3) N-alkylated MCTA's (which may be saturated or unsaturated and may also contain C-alkyl substituents) in which at least one hydrocarbon radical (preferably one containing from about one to twenty carbon atoms) is attached to at least one of the nitrogen atoms in the ring; (4) analogous MCTA's which contain substituted hydrocarbon radicals (preferably amino-nitrogen-containing radicals, such as aminoalkyl or polyaminoalkyl radicals) attached to nitrogen atoms in the ring; and (5) organic or inorganic acid salts of MCTA's that have salt-forming amino groups in the ring or amino-nitrogen-containing hydrocarbon substituents such as aminoalkyl or polyaminoalkyl radicals. Particularly preferred MCTA's contain 14- or 16-membered rings, have six methyl groups attached to ring carbon atoms, and have the remaining valances of the ring carbon and nitrogen atoms satisfied by hydrogen atoms, alkyl radicals, amino-nitrogen-containing alkyl radicals, or the acid salts of such MCTA's.

Solvents for the MCTA's of the present invention can include substantially any liquid which is miscible with and compatible with the MCTA's. As known to those skilled in the art, for certain applications it is desirable that a corrosion inhibitor be dissolved in an aqueous liquid or a preferentially water-miscible liquid, while in other applications the inhibitor should be dissolved in an oil or a preferentially oil-miscible liquid.

For example, in an oil well that produces relatively hot sour gaseous fluids, it is desirable that the corrosion inhibitor be dissolved in an oil or preferentially oil-miscible liquid that will remain substantially immiscible with both the gaseous and aqueous components of the produced fluid. The solution being mixed with the corrosive fluid within the well near the point at which the corrosive fluid enters the well. For use on metal materials contacted by corrosive gaseous products, particularly suitable solvents for the present MCTA's comprise organic liquid solvents which are incompletely miscible with the corrosive fluids. Examples of suitable solvents include liquids (which are liquid at the temperatures and pressures at which the metal materials are to be treated) such as hydrocarbons, alcohols, ketones, ethers, esters, fatty acids (which tend to form the acid salts of the amines without reducing their capability of forming corrosion inhibiting films or metal surfaces) and the like.

The metal treating compositions formed by combining the present MCTA's with a suitable solvent can, where desirable, contain substantially any of the numerous additives that are conventionally used in corrosion inhibitor compositions. Such additives include dispersants, wetting agents, deemulsifying agents, and the like.

EXAMPLE 1

Preparation of a Hexamethylated, Saturated, 14-Membered MCTA

A perchlorate of divalent nickel is prepared by slurrying an anhydrous nickel carbonate in absolute ethanol and adding a slight excess of 70% perchloric acid. After heating, to expel the carbon dioxide, and concentrating the solution by evaporation, the solution can be used as follows to form an amine complex of the nickel perchlorate.

An excess amount (such as 30% more than stoichiometric) of ethylenediamine is added to the nickel perchlorate-containing solution. The solution is refluxed under nitrogen and then cooled. The cooling causes precipitation, with yields in the order of 90% being attainable.

The nickel-amine-perchlorate complex is mixed with pre-dried acetone. Proportions in the order of 1/10th mole of the complex with 150 to 200 milliliters of the acetone are suitable. The resulting solution is heated to its boiling point and irradiated with a GE sun lamp for about 12 hours. Concentration by evaporation leads to the precipitation of a nickel-perchlorate-amine complex in which the amino portion is a hexamethylated, unsaturated MCTA in which a nickel atom is held by chelate bonding.

The amine is released from the nickel-chelating complex by adding the complex to hydrochloric acid and boiling it for several hours. Cooling perciptates the perchloric acid salt of the amine. Filtration and tritation with base releases the free amine.

The saturated, hexamethylated amine is formed by hydrogenating the unsaturated amine, for example, by means of a reaction with sodium borohydride. This MCTA has the skeletal formula:

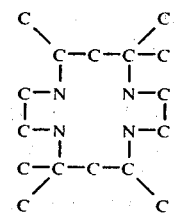

EXAMPLE 2

Corrosion Inhibition Tests of a Hexamethylated, Saturated, 16-Membered MCTA

The tested compound was prepared substantially as described in Example 1; except for using trimethylenediamine in place of ethylenediamine. Comparative tests were made with carbon steel specimens. The specimens were immersed in $H_2S$-saturated oil-water environments at 180°F in bottles that were rotated to agitate their contents.

The effectiveness of the MCTA was compared with that of morpholine, which is a widely-used water-soluble neutralizing amine available from Union Carbide, and that of the filming-amine Kontol K-142, which is a long-chain imidazoline corrosion inhibitor, available from Tretolite Company. At an inhibitor concentration of 50 parts per million (based on the preponderent, 85% volume, oil-phase liquid) this water-soluble MCTA provided 80% protection. It was nearly as effective as the Kontol K-142 which provided 90% protection.

This MCTA was far superior to the morpholine - the other water-soluble amine. An amount in the order of 1,000 parts per million of morpholine was required to obtain an 80% degree of protection.

EXAMPLE 3

Corrosion Inhibition Tests of a Hexamethylated, Saturated, 16-Membered MCTA Containing One Palmityl Radical on Each of Two Ring Nitrogen Atoms A 16-membered MCTA of the type described in Example 2 was amidized by reacting it with palmityl chloride and then reducing the carbonyl group, by a reduction with lithium aluminum hydride. This attached one palmityl group to each of the two ring nitrogen atoms.

In tests similar to those of Example 2, at a concentration of only five parts per million, this MCTA provided 97% protection. At the same concentration, Kontol K-142 provided only 20% protection. On further testing it was found that only 2 parts per million of the MCTA was required to provide 95% protection; whereas 50 parts per million of the Kontol K-142 was required for equal protection.

EXAMPLE 4

Corrosion Inhibition by a Hexamethylated, Saturated, 14-Membered MCTA Containing a 3-Aminopropyl Group on a Ring Nitrogen Atom This MCTA was prepared substantially as described in Example 3 with the exception of: starting with a 14-membered MCTA, and using 1-chloro-3-aminopropane in place of the palmityl chloride.

In corrosion tests similar to those described above, 100 parts per million of this MCTA provided about 92% protection.

EXAMPLE 5

Corrosion Inhibition by a Dioleate Salt of a Cobalt Complex of a Polyaminoalkyl-Substituted, Hexamethylated, Saturated, 14-Membered MCTA This material was prepared by subjecting a 14-membered MCTA of the type described in Example 1 to (a) a hydrogen abstraction with sodium amide and a reaction with 1-bromo-3-aminopropane, to attach a 3-aminopropyl radical to one nitrogen atom, (b) reacting that material with about six moles of ethylene imine, to attach a polyethyleneamine chain to the so-substituted nitrogen atom and (c) refluxing the product (in acetonitrile) with cobaltous dioleate, to provide the tested material.

In corrosion tests similar to those described above, 100 parts per million of this MCTA provided about 92% protection.

EXAMPLE 6

Effect of Temperature on Corrosion Inhibition by a N-Palmityl Substituted MCTA of the Type Described in Example 3

Tests of the types described above were repeated at different temperatures. At 250°F, 2 parts per million of the MCTA provided 65% protection, at 300°F, 2 parts per million provided 50% protection. With a concentration of 100 parts per million, at 300°F, this MCTA provided 70% protection.

EXAMPLE 7

Corrosion Inhibition in Carbon Dioxide-Atmosphere

The N-palmityl substituted 16-membered MCTA of the type described in Example 3 was tested in an oil-water system, substantially as described above, except that the specimens and liquids were maintained at 180°F under a $CO_2$ atmosphere. At a concentration of 100 parts per million, this MCTA provided 90% protection. It required 200 parts per million of Kontol K-118 (which is a commercial oil-soluble corrosion inhibitor, available from Tretolite) to provide the same degree of protection.

In similar tests in which the $CO_2$ atmospheres was replaced by an $H_2S$ atmosphere, 2 parts per million of the MCTA provided the same degree of protection that was provided by 200 parts per million of Kontol K-118.

EXAMPLE 8

Use In Conjunction with Acetylenic Alcohol In Inhibiting Hydrochloric Acid Induced Corrosion of Metal A hexamethylated saturated 16-membered MCTA, of the type described in Example 2, was tested in aqueous 15% by weight hydrochloric acid solutions containing 0.3% by weight propargyl alcohol. The corrosion rates on carbon steel coupons were measured by means of standard, static weight-loss tests, at the indicated temperatures. The MCTA was present in substantially equal molar properties relative to the alcohol. In three-hour tests in which the MCTA was present, at 200°F, the corrosion rates were reduced by 70% and, at 250°F, the corrosion rates were reduced by 80%.

EXAMPLE 9

Corrosion Inhibition at High Pressure and Temperature

Tests were made of the corrosion on carbon steel in the presence of 20% by weight aqueous ammonium chloride under a hydrogen sulfide pressure of 200 psi. The tests were conducted at 350°F and lasted three to 4 days. A saturated, 16-membered MCTA (of the type described in Example 2) at a concentration of 1% by weight, provided 80% protection. And, in the presence of a saturated calcium chloride brine containing iron sulphide (which seriously aggravates corrosion in such a system) the protection was 80% effective, with a 2.5% by weight concentration of the MCTA.

What is claimed is:

1. A process for inhibiting corrosion of corrodible metal material comprising:
    contacting the metal material with an effective amount of a 14-membered or 16-membered macrocyclic tetramine.

2. The process of claim 1 in which the macrocyclic tetramine is a compound in which 4 nitrogen atoms and 10 or 12 carbon atoms are connected into a 14- or 16-membered heterocyclic ring and the remaining valancies on those atoms are satisfied by members of the group consisting of hydrogen atoms, multiple bonds, hydrocarbon radicals, and substituted hydrocarbon radicals.

3. The process of claim 2 in which the macrocyclic tetramine contains 6 methyl groups attached to ring carbon atoms and the remaining valances of the ring carbon and nitrogen atoms are satisfied by members of the group consisting of hydrogen atoms, alkyl radicals, amino-nitrogen-containing alkyl radicals and acid salts of such a macrocyclic tetramine.

4. A method of inhibiting the corrosion of corrodible metal material in or around a well through which a corrosive fluid is produced, comprising:

contacting said metal material with an effective amount of at least one 14-membered or 16-membered macrocyclic tetramine.

5. The method of claim 4 in which the macrocyclic tetramine is a compound in which 4 nitrogen atoms and 10 or 12 carbon atoms are connected into a 14- or 16-membered heterocyclic ring and the remaining valancies on those atoms are satisfied by members of the group consisting of hydrogen atoms, multiple bonds, hydrocarbon radicals, and substituted hydrocarbon radicals.

6. The method of claim 4 in which surfaces of the metal material are coated with macrocyclic tetramine by dissolving the macrocyclic tetramine in a liquid which is incompletely miscible with the corrosive fluid under the conditions existing within the well and mixing the solution with the corrosive fluid within the well near the point at which the corrosive fluid enters the well.

* * * * *